United States Patent [19]

Piechocki et al.

[11] Patent Number: 5,591,350

[45] Date of Patent: Jan. 7, 1997

[54] IODINE DISINFECTION METHOD USING A GASEOUS IODINE TREATED POROUS MEDIUM

[75] Inventors: Duane Piechocki, Pleasantville; Thomas J. Bormann, Melville; Thomas C. Gsell, Glen Head; Frank R. Pascale; Vlado I. Matkovich, both of Glen Cove, all of N.Y.

[73] Assignee: Pall Corporation, East Hills, N.Y.

[21] Appl. No.: 554,757

[22] Filed: Nov. 7, 1995

Related U.S. Application Data

[63] Continuation of Ser. No. 227,876, Apr. 15, 1994, abandoned.

[51] Int. Cl.$^6$ .................. A61L 2/00; A61K 33/18; B01D 37/00

[52] U.S. Cl. .................. 210/764; 210/483; 210/496; 210/501; 210/503; 210/767; 210/806; 422/1; 422/28; 422/37; 424/78.08; 424/667; 604/408

[58] Field of Search ............................ 210/764, 767, 210/645, 651, 483, 488, 489, 496, 501, 806, 503, 508; 422/1, 28, 37; 424/78.08, 78.25, 667, 672; 435/311; 604/4, 7, 408

[56] References Cited

U.S. PATENT DOCUMENTS

| | | |
|---|---|---|
| 3,401,005 | 9/1968 | Katz . |
| 3,817,860 | 6/1974 | Lambert et al. . |
| 4,010,259 | 3/1977 | Johansson . |
| 4,235,230 | 11/1980 | Stephen et al. . |
| 4,314,997 | 2/1982 | Shanbrom . |
| 4,315,919 | 2/1982 | Shanbrom . |
| 4,381,380 | 4/1983 | LeVeen et al. ..................... 525/452 |
| 4,382,862 | 5/1983 | Dillman ........................... 210/668 |
| 4,412,985 | 11/1983 | Shanbrom . |
| 4,594,392 | 6/1986 | Hatch ............................. 525/327.1 |
| 4,597,975 | 7/1986 | Woodward et al. . |
| 4,880,548 | 11/1989 | Pall et al. ......................... 210/767 |
| 4,883,587 | 11/1989 | LeVeen et al. ..................... 210/501 |
| 4,888,118 | 12/1989 | Barnes et al. ...................... 210/668 |
| 4,891,221 | 1/1990 | Shanbrom . |
| 4,915,839 | 4/1990 | Marinaccio et al. ............... 210/500.23 |
| 4,923,620 | 5/1990 | Pall et al. ......................... 210/767 |
| 4,925,572 | 5/1990 | Pall et al. ......................... 210/767 |
| 4,950,256 | 8/1990 | Luther et al. ...................... 604/265 |
| 5,071,648 | 12/1991 | Rosenblatt ....................... 424/78.06 |
| 5,089,146 | 2/1992 | Carmen et al. .................... 210/782 |
| 5,100,564 | 3/1992 | Pall et al. ......................... 210/782 |
| 5,106,500 | 4/1992 | Hembree et al. ................... 210/266 |
| 5,128,149 | 7/1992 | Shanbrom ........................ 424/529 |
| 5,128,150 | 7/1992 | Shanbrom ........................ 424/533 |
| 5,156,973 | 10/1992 | Shanbrom ........................ 436/16 |
| 5,176,836 | 1/1993 | Sauer et al. ....................... 210/670 |
| 5,186,945 | 2/1993 | Shanbrom et al. ................. 424/529 |
| 5,217,627 | 6/1993 | Pall et al. ......................... 210/767 |
| 5,229,012 | 7/1993 | Pall et al. ......................... 210/767 |
| 5,269,924 | 12/1993 | Rochat ........................... 210/445 |
| 5,281,392 | 1/1994 | Rubinstein ....................... 422/28 |
| 5,302,392 | 4/1994 | Karakelle et al. .................. 424/409 |
| 5,333,626 | 8/1994 | Morse et al. ...................... 128/898 |
| 5,360,605 | 11/1994 | Shanbrom ........................ 424/78.08 |
| 5,370,869 | 12/1994 | Shanbrom ........................ 424/78.22 |

FOREIGN PATENT DOCUMENTS

| | | |
|---|---|---|
| 0382018 | 8/1990 | European Pat. Off. . |
| 0526678 | 2/1993 | European Pat. Off. . |
| 8502422 | 6/1985 | WIPO . |
| 9104088 | 4/1991 | WIPO . |
| 9204031 | 3/1992 | WIPO . |
| 9204061 | 3/1992 | WIPO . |
| 9207656 | 5/1992 | WIPO . |
| 9304731 | 3/1993 | WIPO . |
| 9304730 | 3/1993 | WIPO . |
| 9304678 | 3/1993 | WIPO . |
| 9306911 | 4/1993 | WIPO . |
| 9317693 | 9/1993 | WIPO . |
| 9321933 | 11/1993 | WIPO . |
| 9325268 | 12/1993 | WIPO . |
| 9400161 | 1/1994 | WIPO . |
| 9400011 | 1/1994 | WIPO . |
| 9406289 | 3/1994 | WIPO . |
| 9409635 | 5/1994 | WIPO . |

OTHER PUBLICATIONS

Chapman, J. et al. "Inactivation of virus in blood products with iodized starch." (S268). Transfusion. vol. 32 Supplement. Conference Abstracts—45th Annual Mtg. of the American Assoc. of of Blood Banks; San Francisco, CA; Nov. 7–12, 1992.

Primary Examiner—John Kim
Attorney, Agent, or Firm—Leydig, Voit & Mayer

[57] ABSTRACT

Methods, systems and devices for processing fluid provide for contacting the fluid with iodine.

15 Claims, No Drawings

IODINE DISINFECTION METHOD USING A GASEOUS IODINE TREATED POROUS MEDIUM

This disclosure is a continuation of patent application Ser. No. 08/227,876, filed Apr. 15, 1994 now abandoned.

TECHNICAL FIELD

This invention relates to the use of a halogen in connection with disinfection or sterilization. More particularly, the invention relates to the use of iodine treated media in connection with processing a biological fluid.

BACKGROUND OF THE INVENTION

The presence of deleterious or undesirable material, e.g., potentially pathogenic viruses and/or microorganisms such as bacteria, is of great concern during many protocols, particularly those involving surgery, testing of bodily fluids, and/or cell culturing. For example, the introduction of disease causing material such as microorganisms and/or endotoxins into a patient, e.g., through administration of a contaminated fluid, or by a failure to follow strict aseptic techniques during invasive procedures, may have serious, and possibly fatal, ramifications for the patient. Additionally, those who handle the contaminated fluid and/or care for the patient may also face health risks resulting from exposure to the pathogens. Furthermore, the presence of microorganisms may adversely affect cell cultures and/or pose a health threat to laboratory technicians who handle the contaminated fluid or the fluid processing equipment.

While a number of procedures and/or reagents for inactivating and/or killing microorganisms are known, they have suffered from a number of deficiencies, including toxicity to the patient and/or adverse affects on the disinfected or sterilized fluid. Moreover, some other procedures and/or reagents, for example, including those disclosed in International Publication Nos. WO 92/04031, WO 93/06911, and WO 92/04061, require a sophisticated, labor intensive effort to carry out disinfection safely and effectively, and they may not be suitable for a wide variety of protocols.

There are other protocols that involve the removal or depletion of deleterious or undesirable material that could be beneficially combined with a disinfection and/or sterilization protocol. For example, with respect to bodily fluids such as blood, since blood and blood components may include varying numbers of white blood cells (leukocytes), which may cause undesirable effects when administered to a patient, blood processing techniques may also include leukocyte depleting the blood or blood components, e.g., by passing the blood or blood components through a leukocyte depletion device. Since blood may also include potentially pathogenic microorganisms such as bacteria, e.g., *Yersinia enterocolitica*, and/or viruses, it would be advantageous to provide a sterilization procedure that is compatible with a leukocyte depletion protocol.

Accordingly, there is an unaddressed need in the art for a method and system that is suitable for a wide variety of microorganism and/or virus elimination, reduction, or inactivation protocols. Additionally, there is a need for a contamination reduction protocol that is easy to carry out, and does not require extensive training of the personnel who will be carrying out the protocol. Moreover, it would be desirable to provide a disinfection and/or sterilization method and system that is compatible with other protocols, especially blood processing protocols.

These and other advantages of the present invention will be apparent from the description as set forth below.

SUMMARY OF THE INVENTION

In accordance with the present invention, a disinfection and/or sterilization environment is provided such that potential pathogens, e.g., viruses and/or microorganisms such as bacteria, that may enter the environment or be present in the environment, are exposed to at least one halogen, preferably iodine, more preferably iodine immobilized in or on a porous medium, to kill or inactivate the microorganisms and/or viruses. For example, microorganisms and/or viruses may contact immobilized iodine as they pass through a porous medium, and this contact provides for a virucidal and/or a bacteriocidal effect.

In another embodiment, the present invention provides for an environment such that microorganisms and/or viruses that may enter the environment or be present in the environment, are exposed to iodine, and this exposure is sufficient to prevent growth and/or multiplication of the microorganisms and/or viruses. For example, the present invention provides for a bacteriostatic and/or virustatic environment.

The present invention provides a contamination elimination, reduction, or inactivation protocol that is easy to use. The present invention may be used wherever a disinfected, sterile or antiseptic environment would be desirable. In a preferred embodiment, the present invention provides a disinfection and/or sterilization protocol that is easily compatible with other protocols, especially blood processing protocols.

SPECIFIC DESCRIPTION OF THE INVENTION

According to the present invention, a method for disinfecting and/or sterilizing fluid is provided comprising contacting the fluid with a halogen, preferably iodine, which is immobilized in or on a medium. Preferably, the method includes passing a liquid through a iodine-containing porous medium. In some embodiments, the method may include removing iodine from the liquid. For example, the iodine-containing liquid may be contacted with an iodine removing or binding material, e.g., at least one of polyvinyl pyrrolidone, starch, and carbon, to separate iodine from the liquid. In some embodiments, iodine may be removed by sieving.

The present invention includes a method for treating a biological fluid comprising contacting the fluid with iodine, and removing leukocytes from the fluid. Leukocytes may be removed before, after, and/or while contacting the biological fluid with iodine. In a preferred embodiment, the biological fluid is passed through a porous medium having iodine immobilized in or on the porous medium. The method may include sterilizing the biological fluid. A method in accordance with the invention may also include separating iodine from the biological fluid.

In accordance with the invention, a method for processing a fluid comprises passing the fluid through a gaseous halogen treated porous medium. Preferably, the method comprises passing a biological fluid through a gaseous iodine treated porous medium. The method may also include removing leukocytes from a fluid, before, after, and/or while passing the fluid through the iodine treated porous medium. For example, the method may include passing a biological fluid through a gaseous iodine treated porous medium, and passing the fluid through a porous leukocyte depletion medium. In some embodiments, the method may include passing the biological fluid through a porous gaseous iodine treated leukocyte depletion medium.

The present invention provides a device for processing a fluid comprising a porous medium including iodine; and at least one iodine removing or binding material. Preferably, the iodine removing or binding material is at least one of polyvinyl pyrrolidone, starch, and carbon. Preferably, the device is suitable for processing a biological fluid, and comprises a fibrous porous medium including two or more layers; having iodine immobilized in or on one layer, and at least one of polyvinyl pyrrolidone, starch, and carbon in or on another layer. In a preferred embodiment, the device comprises a housing and a fibrous porous medium; wherein the housing includes an inlet and an outlet and the porous medium is interposed between the inlet and the outlet and across the fluid flow path. The device may also be suitable for depleting leukocytes from a biological fluid.

In accordance with the invention, a device for processing a fluid comprises a gaseous halogen treated element. The element is preferably porous, and the gaseous halogen is preferably iodine.

The present invention also provides a device for processing a fluid comprising a porous medium having iodine immobilized in or on the porous medium, including iodine bound to an iodine binding polymer. In one embodiment, a device in accordance with the invention comprises a synthetic fibrous porous medium, including iodine complexed with polyvinyl pyrrolidone.

In accordance with the invention, microorganisms and viruses refer to both non-pathogenic, and, more preferably, pathogenic, organisms and viruses. As used herein, microorganisms refer to bacteria, including gram positive and gram negative bacteria; viruses, include but are not limited to herpesvirus, e.g., the alpha, beta, and gama subfamilies, which include herpes virus simplex 1, 2, 3, 4, and 5, exemplified by cytomegalovirus (CMV), and Epstein-Barr virus (EBV). Other viruses include hepatitis, human immunodeficiency virus (HIV), simian immunodeficiency virus (SIV), and hepatitis. Microorganisms include protozoans, which include but are not limited to Trypanosoma spp., as well as Plasmodium spp. such as *P. falciparum, P. malariae, P. ovale,* and *P. vivax*; bacteria such as *Yersinia enterocolitica*; Campylobacter spp.; Shigella spp.; Salmonella spp.; *Staphylococcus epidermis*; and *Legionella pneumonophilia*; fungi, and yeasts.

The present invention is suitable for any protocol wherein a disinfection, sterilization, antiseptic, and/or germicidal environment is desirable. Accordingly, any gas or liquid that potentially contains contaminating pathogens such as viruses and/or microorganisms is exposed to a halogen, preferably iodine, to eliminate, reduce, or inactivate contaminants that may be present. The present invention is compatible with both closed and open systems.

While the invention is particularly applicable to the treatment of bodily fluids, such as, but not limited to blood and semen, it is also suitable for treatment of parenteral fluids such as, for example, saline, medicament solutions, nutrient solutions, various intravenous solutions and the like.

In accordance with the invention, the following may also be treated: milk; tissue; cell cultures, including cell culture products, reagents, solutions and/or preparations; preservatives; additives; and diagnostic test reagents. The present invention is suitable for both human and veterinary applications, including those involving therapy and diagnosis.

In the most preferred embodiment, the present invention provides for treatment of a biological fluid. In accordance with the invention, biological fluid includes any treated or untreated fluid associated with living organisms, particularly blood, including whole blood, warm or cold blood, and stored or fresh blood; treated blood, such as blood diluted with a physiological solution, including but not limited to saline, nutrient, and/or anticoagulant solutions; one or more blood components, such as platelets suspended in plasma, platelet concentrate (PC), platelet-rich plasma (PRP), platelet-free plasma, platelet-poor plasma (PPP), plasma, packed red cells (PRC), transition zone material, buffy coat; analogous blood products derived from blood or a blood component or derived from bone marrow; red cells suspended in physiological fluid; and platelets suspended in physiological fluid. The biological fluid may include leukocytes, or may be treated to remove leukocytes. As used herein, biological fluid refers to the components described above, and to similar blood products obtained by other means and with similar properties.

Halogens refer to fluorine, chlorine, bromine, astatine, and, in the preferred embodiment of the invention, iodine. In accordance with the invention, iodine refers to molecular iodine, I, or diatomic iodine, $I_2$, or other forms of iodine that include iodine available in molecular or diatomic form, e.g., in an iodine-containing complex, mixture, compound, solution, or preparation. The iodine may be utilized with a solubilizing agent and/or a carrier. The iodine may be present as part of a complex, for example, but not limited to, a complex with polyethylene glycol mono(nonylphenyl)ether, or polyvinyl pyrrolidone (PVP). In one embodiment, the polyvinyl pyrrolidone is suitable for use in physiologically acceptable solutions, e.g., povidone (USP), and is complexed with iodine to form povidone-iodine.

In those embodiments including the use of PVP-iodine complexes, PVP may be utilized in a variety of forms, e.g., a solid such as a crystal or a powder; a solution, an emulsion, a suspension, or an aerosol. For example, PVP may be dissolved in an aqueous solution, or it may be used in a form that swells in aqueous solution to form a substantially water insoluble povidone-iodine composition. In one embodiment, the PVP-iodine complex is bound to a porous medium. The PVP-iodine complex may be bound in or on the porous medium.

In a preferred embodiment, the invention provides for immobilizing the iodine in or on a medium, so that microorganisms and/or viruses in the fluid or the liquid contacting the iodine are killed or inactivated as they contact and/or pass through or along the medium. The use of immobilized iodine may minimize or eliminate the need for subsequently removing the iodine from the liquid.

However, in some embodiments, the iodine remains in contact with liquid. For example, iodine may be released as the biological fluid contacts and/or passes through the medium. Alternatively, for example, in those embodiments wherein the iodine is not immobilized in or on a porous medium, iodine may have been added to the liquid, or the liquid may have been placed in contact with insoluble PVP-iodine particles. In these embodiments, i.e., involving iodine in the treated fluid, the invention may provide for, if desired, separating, scavenging or removing the iodine from the fluid, e.g., by sieving, filtering, and/or using an iodine separating or binding material.

The iodine may be separated, scavenged or removed directly or indirectly. Illustratively, iodine may be directly removed by placing the iodine-containing fluid in contact with an iodine binding material or medium such as an affinity or separating medium, e.g., a medium containing at least one of carbon, preferably activated carbon, starch and polyvinyl pyrrolidone, to remove the iodine from the fluid. The iodine may form a complex with the iodine binding material to allow the iodine to be removed from the fluid. For example, an iodine-containing fluid may be passed through a porous medium including an iodine binding material, to provide for iodine removal as the fluid passes through the medium.

In other embodiments, this iodine may be indirectly removed from the fluid, e.g., by sieving or filtering. For example, one technique for separating or removing iodine indirectly includes sieving insoluble PVP-iodine particles from the fluid by passing the PVP-iodine-containing fluid through a porous medium of a suitable pore structure to entrap the PVP-particles as the fluid passes through the porous medium.

In accordance with the invention, a medium such as a porous medium, more preferably a porous medium comprising synthetic fibers, may be treated with iodine to provide iodine immobilized in or on the medium. In some embodiments, the iodine may be embedded or entrapped within the medium. In other embodiments, the medium may be substantially non-porous, for example, but not limited to, at least one of a container, a housing, a conduit, a connector, a valve, and a cannula. Preferable porous media include those suitable for processing biological fluids, including leukocyte depletion media. Other suitable porous media include, but are not limited to those used in processing nutrient and/or medicament solutions, and for passing gas, e.g., gas inlets and/or gas outlets.

The medium may be exposed to iodine in solid, liquid, or gaseous form. The iodine may be immobilized by, for example, at least one of complexation, adsorption, chemical bonding, coating, and gas plasma treatment. A variety of techniques for immobilizing iodine are suitable. Preferably, the medium is exposed to iodine in gaseous form.

For example, iodine may be converted into gaseous form during sublimation to produce a suitable iodine-containing medium. Illustratively, the iodine may be placed in a container including the medium to be treated, and the iodine may then be heated at a suitable temperature as is known in the art. The container may be allowed to cool before removing the iodine treated medium.

In some embodiments, after iodine is exposed to the gaseous iodine, air or gas may be passed through the container, e.g., over the treated medium, to allow excess iodine to be removed before allowing the medium to cool. The air or gas may be warmed or heated before entering the container, and the treated medium may be cooled to room temperature before removing it from the container. This may be desirable for those embodiments providing for decreased iodine release after contacting the iodine with a fluid to be treated.

The medium may be exposed to the iodine at any point during the manufacture of the medium. For example, the medium may be produced by melt blowing of fibers, and the fibers may be exposed to iodine during the melt blowing process. Alternatively, the medium may be mixed with iodine during the solubilization of the material used in making the medium. In yet another embodiment, a medium may be manufactured and then exposed to iodine.

If desired, the medium may be exposed to iodine and stored before use. Preferably, the iodine treated medium is placed in a suitable container, e.g., an opaque container such as brown plastic or glass container, or an aluminized bag, before storage. Among other advantages, the use of such containers may decrease the chance of iodine oxidation.

Fibrous media may be particularly suitable for exposure to iodine as the fibers may provide an increased surface area to maximize contact with the fluid to be disinfected. Porous membranes are also suitable for exposure to iodine in accordance with the invention.

While the medium suitable for exposure to iodine may be produced from any suitable material compatible with the fluid to be treated, commercially available materials are preferred. The fluid treatment media of this invention may be preferably formed, for example, from any natural or synthetic material capable of forming fibers or a membrane. Suitable polymers include, but are not limited to, polyolefins, polyesters, polyamides, polysulfones, acrylics, polyacrylonitriles, polyaramides, polyarylene oxides and sulfides, and polymers and copolymers made from halogenated olefins and unsaturated nitriles. Examples include, but are not limited to, polyvinylidene difluoride (PVDF), polyethylene, polypropylene, polybutylene terephthalate (PBT), polyethylene terephthalate (PET), and any nylon, e.g., Nylon 6, 11, 46, 66, and 610. Preferred polymers are polyolefins, polyesters, and polyamides. Especially preferred is polyester.

Suitable materials include polymeric spheres to which iodine can be bound. Other suitable materials include cellulosic derivatives, such as cellulose acetate, cellulose propionate, cellulose acetate-propionate, cellulose acetate-butyrate, and cellulose butyrate. Non-resinous materials, such as glass fibers, may also be used.

In accordance with the invention, the surface characteristics of the medium, e.g., a fiber or a membrane, may be modified by chemical reaction including wet or dry oxidation, by coating or depositing a polymer on the surface, or by a grafting reaction. Grafting reactions may be activated by exposure to an energy source such as gas plasma, heat, a Van der Graff generator, ultraviolet light, or to various other forms of radiation, or by surface etching or deposition using a gas plasma treatment. The medium may be treated to modify the critical wetting surface tension (CWST).

A variety of materials and devices are suitable for separating iodine from a fluid and may be used in accordance with the invention. In one embodiment, the iodine separating medium may comprise the materials listed above. For example, the iodine separating medium may comprise polymers such as polyolefins, polyesters, and polyamides, including nylon and PBT.

In some embodiments, the material listed above, e.g., nylon, may provide for separating iodine without an additional iodine binding material. In other embodiments, the iodine separating medium may also include an iodine separating or binding material. For example, a medium comprising the materials listed above may be combined with at least one of carbon, starch and polyvinyl pyrrolidone (PVP). Accordingly, a medium may be treated, e.g., by a grafting reaction, in order to include at least one of carbon, starch and PVP to provide a suitable iodine separating medium. Illustratively, commercially available grades of starch, e.g., amylose, and polyvinyl pyrrolidone, e.g., povidone, in soluble or insoluble form, are suitable for the iodine separating medium.

In some embodiments, at least one of starch, PVP, and carbon, preferably activated carbon, may be suitable with or without the other materials listed above. For example, the iodine removing medium may comprise carbon fibers, or a bed of particles comprising at least one of carbon, PVP, and starch. Preferably, commercially available media including carbon, PVP, and/or starch are utilized. Suitable carbon media include activated carbon media, e.g., activated carbon particles, felts, fibers, cloths, and paper. Examples of commercially available activated carbon media include those Kuractive® media, available from Kuraray Chemical Company, Ltd., Japan, and media available from Calgon Carbon Corporation, Pittsburgh, Pa.

In some embodiments, to confine the particles, the bed of particles may be upstream of a particle supporting medium such as nylon or PBT, or the bed may interposed between layers of media.

In other embodiments, the iodine separating medium may also include iodine. For example, carbon, starch and/or PVP may be combined with iodine. In these embodiments, fluid may be placed in contact with the iodine, and, if iodine is released, or the fluid otherwise contains iodine, the iodine may be separated from the fluid upon contact between the iodine and the iodine binding material, e.g., activated carbon, starch or PVP.

A leukocyte depletion medium which may be used in accordance with the present invention comprises a porous medium suitable for depleting leukocytes from the fluid passing through the leukocyte depletion medium. Exemplary leukocyte depletion media include but are not limited to those disclosed in U.S. Pat. Nos. 5,217,627, 5,100,564 and 4,880,548 as well as International Publication Nos. WO 92/07656 and WO 91/04088. Additional exemplary leukocyte depletion media include those disclosed in U.S. Pat. Nos. 4,925,572, 4,923,620, and 5,229,012. These U.S. patents and International Publications also disclose exemplary housings for the leukocyte depletion media.

In accordance with the invention, a gas or liquid that may contain contaminating pathogens such as viruses and/or microorganisms is exposed to a halogen, preferably iodine, to eliminate, reduce, or inactivate contaminants that may be present. For example, the fluid to be treated is placed in contact with iodine immobilized in or on a medium, and microorganisms and/or viruses that may be present are inactivated and/or killed.

In a preferred embodiment, a fluid, even more preferably, a biological fluid, is passed through a porous medium including iodine immobilized in or on the medium, so that microorganisms and/or viruses that may be present in the fluid are placed in contact with the immobilized iodine. In another embodiment, fluid may be placed in a container along with a medium including iodine immobilized in or on the medium. This allows at least a portion of the fluid to contact the immobilized iodine. If desired, the container, for example, a flexible container such as a conventional blood bag, may be manipulated, e.g., compressed and/or rotated, to increase the efficiency of contact. In these embodiments, the contact between the microorganisms an/or viruses and the iodine is sufficient to inactivate and/or kill the microorganisms and/or viruses.

In some embodiments, separate portions of fluid may be processed differently. For example, in those embodiments including processing a biological fluid such as whole blood, at least one portion or component, e.g., platelet-rich plasma, may be passed through an iodine-containing medium, without passing another portion or component, e.g., red cells, therethrough. If desired, a portion or component that was exposed to iodine may be recombined with an unexposed portion. For example, plasma may be passed through an iodine-containing medium, and then combined, e.g., mixed, with red cells that were not passed through an iodine-containing medium.

In accordance with the invention, the contact time between the fluid and the iodine and/or the iodine concentration may be varied to provide a desirable effect. Illustratively, the fluid may be recirculated to repeatedly provide contact with the iodine treated medium, or the fluid may be placed in contact with a series of two or more iodine treated media, which may include different iodine concentrations. In another embodiment, the flow rate may be varied to provide less or more contact time with the iodine. The method may include providing different or repeated contact times and/or iodine concentrations for a desired result. For example, a first contact time and/or concentration may be utilized to provide one desired result, e.g., a virustatic or bacteriostatic effect, and a second contact time and/or concentration may be utilized to provide another desired result, e.g., a virucidal or bacteriocidal effect.

As noted earlier, in some embodiments it may be desirable to scavenge or filter the iodine from the fluid. While a variety of techniques and reagents may be useful, in a preferred embodiment, the iodine-containing fluid is exposed to at least one of starch, PVP, and carbon to remove the iodine from the fluid. In a more preferred embodiment, the fluid is passed through a porous medium including starch, PVP, or activated carbon to remove the iodine.

In some embodiments, the method may include passing the fluid through separate iodine-containing and iodine removing devices. In other embodiments, fluid may be passed through a single device that provides for exposing the fluid to iodine, and separating iodine from the fluid. For example, the fluid may be passed through a device including multiple layers and/or multiple porous media, wherein at least one layer and/or medium includes iodine, and at least one layer and/or medium includes starch or carbon.

In a preferred embodiment, wherein a biological fluid is exposed to iodine, the method includes leukocyte depleting the biological fluid, e.g., by passing the fluid through a leukocyte depletion device. Leukocytes may be removed before, after, or during contact of the biological fluid with iodine. In those embodiments including separating iodine from the fluid, leukocytes may be removed before, after, or during removal of iodine from the biological fluid.

Accordingly, the method may include passing the fluid through a leukocyte depletion device during an extracorporeal protocol, e.g., open heart surgery, apheresis, cardioplegia; and/or during blood banking protocols, e.g., leukocyte depletion of blood components before storage. Of course, the instant invention is also compatible with non-leukocyte depleting extracorporeal and/or blood banking protocols.

In some embodiments, the method may include "replenishing" the iodine in or on the medium. For example, during long term continuous use, the medium may have the potential to exhibit reduced efficiency, since iodine may be released over a period of time. Accordingly, it may be desirable to treat the medium with additional iodine. Illustratively, iodine may be added in solution and passed through a porous medium to replenish the lost iodine and/or regenerate the virucidal and/or bacteriocidal effect.

In a preferred embodiment, wherein a biological fluid is placed in contact with the iodine, the use of the iodine does not interfere with additives to the biological fluid. Illustratively, a biological fluid such as whole blood or a blood component may be placed in contact with immobilized iodine without interfering with the action of, for example, at least one of ethylene diamine tetraacetic acid, acid citrate dextrose, and heparin.

EXAMPLES

Example 1.

Four discs of leukocyte depletion media are prepared in accordance with U.S. Pat. No. 4,925,572. Each disc includes a laminate of layers of melt blown PBT fibers having an average fiber diameter of about 2.4 microns.

The discs, spaced apart from each other, are placed on a perforated wire mesh porcelain grid of about 8.5 inches in diameter in a glass desiccator along with about 7–10 grams of iodine crystals (99.99% purity, reagent grade, Aldrich Chemical Co., Inc.) at the bottom of the desiccator. The iodine crystals are distributed in a monolayer in the bottom of the desiccator, which has a diameter of about 5.5 inches. The grid is located approximately 2 inches above the crystal monolayer. The desiccator is sealed, placed in an oven and heated to 50°C. for 16 hours, during which time the iodine sublimes and reacts with the discs, giving them a reddish brown color.

The desiccator is removed from the oven and allowed to cool at ambient temperature. The discs are removed from the desiccator and sealed in aluminized bags.

One iodine treated disc is placed in a plastic jig. A unit of leukocyte depleted PRP, approximately 250 ml, is bacterially challenged with *Serratia marcesens*. A sample of the "spiked" PRP is determined to have a CFU/ml of about $2.7 \times 10^6$/ml. The PRP is passed through the disc at a flow rate of about 2 cc/min.

The effluent is collected, and a viable cell count is determined. In summary, a series of dilutions, i.e., $10^{-5}$, $10^{-4}$, $10^{-3}$, $10^{-2}$, and $10^{-1}$, are prepared, and a drop of PRP from each dilution is placed on a different agar plate, spread, and the plates are incubated. The viable cell count is taken after 24 hours. The CFU/ml for each of the dilutions after 24 hours is 0/ml. The results of this Example show that PRP is sterilized after passing it through a gaseous iodine treated porous medium.

While the invention has been described in some detail by way of illustration and example, it should be understood that the invention is susceptible to various modifications and alternative forms, and is not restricted to the specific embodiments set forth. It should be understood that these specific embodiments are not intended to limit the invention but, on the contrary, the intention is to cover all modifications, equivalents, and alternatives falling within the spirit and scope of the invention.

We claim:

1. A method for processing a biological fluid comprising:
   passing the biological fluid into a flexible container comprising a blood bag, said container including a gaseous iodine treated porous medium;
   contacting the gaseous iodine treated porous medium with the fluid.

2. The method of claim 1 further comprising separating iodine from the fluid.

3. The method of claim 1 including removing leukocytes from the fluid.

4. The method of claim 1 wherein contacting the medium with the fluid depletes leukocytes from the fluid.

5. The method of claim 4 wherein contacting the gaseous iodine treated porous medium with the fluid comprises passing the fluid through a gaseous iodine treated fibrous porous medium.

6. The method of claim 4 wherein passing the fluid through the gaseous iodine treated porous medium comprises passing the fluid through a gaseous iodine treated synthetic polymeric fibrous medium, said medium including at least one of polybutylene terephthalate, and polyethylene terephthalate.

7. The method of claim 1 further comprising contacting the fluid with an iodine separating medium.

8. The method of claim 7 wherein contacting the fluid with an iodine separating medium comprises passing the fluid through a porous medium including at least one of nylon, carbon, starch, and polyvinyl pyrrolidone.

9. The method of claim 1 wherein contacting the gaseous iodine treated porous medium with the fluid comprises passing the fluid through a gaseous iodine treated fibrous porous medium.

10. The method of claim 9 wherein the gaseous iodine treated fibrous porous medium comprises a synthetic polymeric medium, and the method further comprises passing the fluid through a porous iodine separating medium.

11. The method of claim 1 wherein passing the fluid through the gaseous iodine treated porous medium comprises passing the fluid through a gaseous iodine treated synthetic polymeric fibrous medium, said medium including at least one of polybutylene terephthalate, and polyethylene terephthalate.

12. The method of claim 1 further comprising administering the fluid to a patient.

13. The method of claim 1 wherein the biological fluid comprises platelet-rich plasma.

14. A device for processing a biological fluid comprising:
    a flexible container comprising a blood bag, said container including a gaseous iodine treated porous medium.

15. The device of claim 14 wherein the gaseous iodine treated porous medium comprises a synthetic polymeric fibrous medium, said medium including at least one of polybutylene terephthalate, nylon, and polyethylene terephthalate.

* * * * *